(12) United States Patent
Messas

(10) Patent No.: US 8,317,694 B2
(45) Date of Patent: Nov. 27, 2012

(54) PARIETAL ANCHORING TOOL AND DEVICE, IN PARTICULAR FOR LAPAROSCOPIC OR COELIOSCOPIC SURGERY

(76) Inventor: Aurel Messas, Paris (FR)

( * ) Notice: Subject to any disclaimer, the term of this patent is extended or adjusted under 35 U.S.C. 154(b) by 623 days.

(21) Appl. No.: 11/658,697

(22) PCT Filed: Jul. 27, 2005

(86) PCT No.: PCT/FR2005/001967
§ 371 (c)(1),
(2), (4) Date: Jan. 29, 2007

(87) PCT Pub. No.: WO2006/018546
PCT Pub. Date: Feb. 23, 2006

(65) Prior Publication Data
US 2009/0192527 A1 Jul. 30, 2009

(30) Foreign Application Priority Data
Jul. 27, 2004 (FR) ..................................... 04 08299

(51) Int. Cl.
*A61N 1/362* (2006.01)
(52) U.S. Cl. ........... 600/218; 600/37; 600/201; 606/151
(58) Field of Classification Search ............ 600/37, 600/201–209, 217, 218; 606/151, 157
See application file for complete search history.

(56) References Cited

U.S. PATENT DOCUMENTS

| 3,274,658 | A | | 9/1966 | Pile | |
|---|---|---|---|---|---|
| 4,602,631 | A | * | 7/1986 | Funatsu | 606/142 |
| 5,242,456 | A | * | 9/1993 | Nash et al. | 606/142 |
| 5,954,057 | A | | 9/1999 | Li et al. | |
| 6,210,418 | B1 | * | 4/2001 | Storz et al. | 606/142 |
| 7,112,172 | B2 | * | 9/2006 | Orban et al. | 600/209 |
| 2003/0167055 | A1 | | 9/2003 | Kolata et al. | |
| 2004/0116949 | A1 | | 6/2004 | Ewers et al. | |

FOREIGN PATENT DOCUMENTS
WO  WO 95/26170  10/1995
* cited by examiner

*Primary Examiner* — Charles A Marmor, II
*Assistant Examiner* — Carrie R Dorna
(74) *Attorney, Agent, or Firm* — Young & Thompson

(57) ABSTRACT

The invention relates to a tool for parietally anchoring a living being's organ (70) comprising means (12, 16, 24) for anchoring said organ, means (36) for fastening at least one pulling element (37) to said anchoring means, wherein said pulling element is fixable to the abdominal wall of said living being in such a way that it makes it possible to lift and keep in suspended position the organ anchored by anchoring means (12, 16, 24) in order to display an anatomical structure during a surgical intervention, in particular in laparoscopy or coelioscopy. The inventive tool also comprises means (14, 22, 28, 38) for grasping and manipulating said anchoring means by a surgical clip. The size of the tool is selected in such a way that it is enabled to pass through a laparoscopic or coelioscopic trocar. A parietally anchoring device is also disclosed.

4 Claims, 5 Drawing Sheets

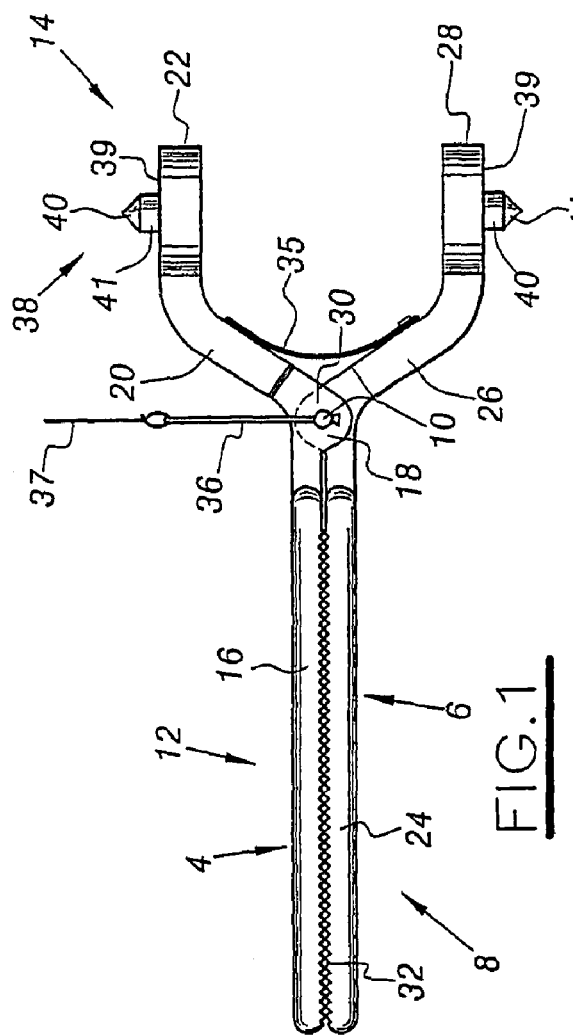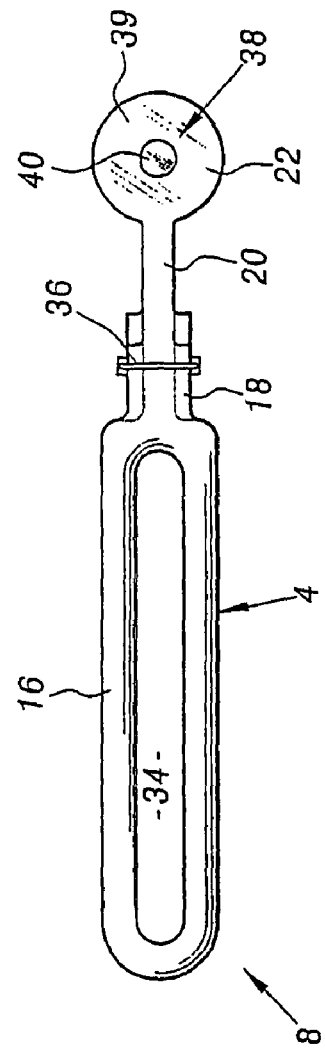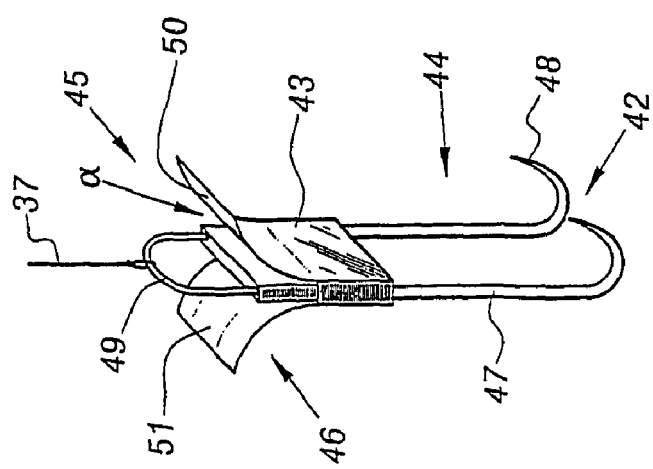

PARIETAL ANCHORING TOOL AND DEVICE, IN PARTICULAR FOR LAPAROSCOPIC OR COELIOSCOPIC SURGERY

FIELD OF THE INVENTION

The invention relates to an instrument for parietally anchoring an organ of a living being, for use in order to expose an anatomical structure during a surgical operation, in particular using laparoscopy or celioscopy.

BACKGROUND OF THE INVENTION

In order to perform surgery using laparoscopy or celioscopy, it is known to artificially inflate the abdomen of a human being or an animal on which an operation is to be performed, and then to introduce trocars through the abdominal wall so as to create sealed entry ports to the operation space.

The anatomical region on which an operation is to be performed is viewed by the surgeon using a special camera introduced into the operation space through a trocar. The anatomical region on which an operation is to be performed is exposed by one or two surgeon's assistants who move away the organs that are located in front of the operation region, using clips, spatulas, or hooks. Thus it is necessary for a surgeon and one or two assistants to be present in order to operate on a patient using laparoscopy.

In some operations, a surgeon's assistant can be replaced by a robotic arm. However, robotic arms are expensive to purchase, they require maintenance, and they are liable to break down.

SUMMARY OF THE INVENTION

An object of the invention is to propose an inexpensive instrument suitable for replacing a surgeon's assistant or a robotic arm when performing surgery by laparoscopy or celioscopy.

Moreover, an anatomical structure can be exposed using surgical forceps passing through the abdominal wall via trocars implanted therein. Thus, five to seven trocars can be implanted in the abdominal wall. Implanting each trocar requires an incision to be made in the abdominal wall.

Another object of the invention is to limit the number of trocars implanted, so as to reduce the number of scars that result from an operation.

To this end, the invention provides a parietal anchor instrument of the above-specified type, for anchoring a human or animal organ, characterized in that it comprises:
holding means for holding said organ;
attachment means for attaching at least one traction element to said holding means, the traction element being suitable for being secured to an abdominal wall of said living being in order to raise said organ held by the holding means and keep it in suspension in order to expose an anatomical structure during a surgical operation, in particular using laparoscopy or celioscopy; and
gripping and manipulation means for gripping and manipulating said holding means with surgical forceps, the dimensions of the instrument being selected to enable it to pass through a laparoscopy or celioscopy trocar.

In particular embodiments, the parietal anchor instrument includes one or more of the following characteristics:
two longitudinal elements hinged to each other about a middle hinge pin to form a clip, and said clip presents, on either side of the hinge pin, firstly said holding means, and secondly said means for gripping the instrument;
it further comprises a spring secured to at least one longitudinal element and urging said holding means towards a rest position that is closed;
the grip means comprise two bearing disks each secured to a respective longitudinal element and provided with a projection on its outside face in order to make the instrument easier to grip by means of a surgical forceps;
the attachment means for attaching a traction element are formed at the hinge pin interconnecting the two longitudinal elements;
the holding means comprise a single or multiple hook;
the means for attaching a traction element comprise an element that defines a closed passage;
said element is secured to a portion of the instrument and forms a projection therefrom; and
the means for attaching a traction element comprise at least one orifice passing through a portion of the instrument.

The invention also provides a device for parietally anchoring an organ, which device comprises at least one traction element and a parietal anchor instrument for anchoring an organ, said traction element being suitable for passing through the abdominal wall and for being secured firstly to the attachment means of said instrument located inside the abdominal wall, and secondly to fastener means outside the abdominal wall so as to form a stationary anchor point for the organ held suspended by the anchor instrument and the traction element

BRIEF DESCRIPTION OF THE DRAWINGS

The invention can be better understood on reading the following description given purely by way of example and made with reference to the accompanying drawings, in which:

FIG. 1 is a diagrammatic side view of a parietal anchor instrument in a first embodiment of the invention;

FIG. 2 is a plan view of the instrument shown in FIG. 1;

FIG. 3 is a diagrammatic perspective view of a parietal anchor instrument in a second embodiment of the invention.

DETAILED DESCRIPTION OF EMBODIMENTS

Figure 4:
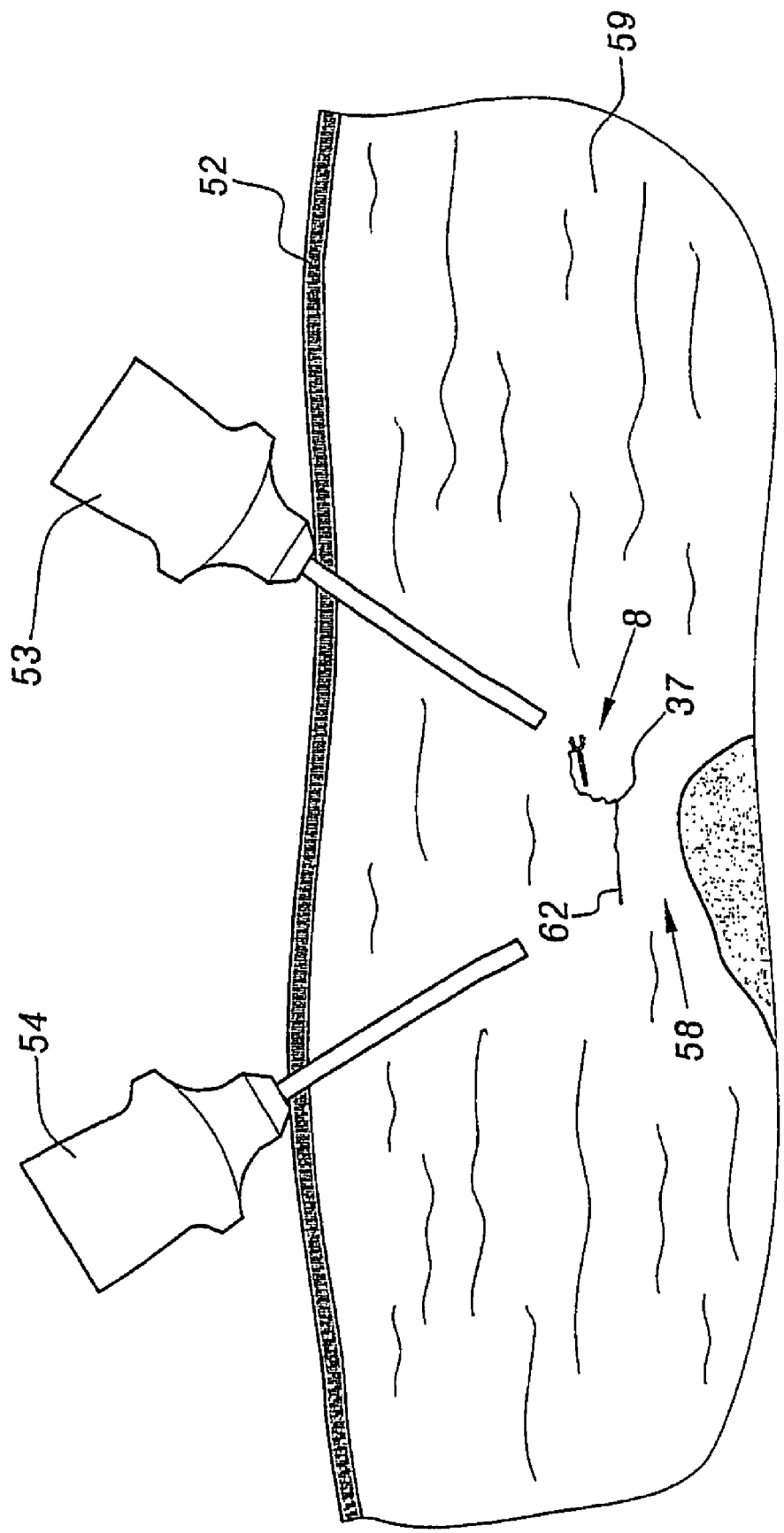
FIGS. 4 to 7 are diagrammatic section views of a region of the abdomen during various steps of a method of parietal anchoring by means of an anchor instrument constituting the first embodiment of the invention.

The parietal anchor instrument shown diagrammatically in FIGS. 1 and 2 comprises a clip. It has first and second longitudinal elements 4 and 6, each made as single piece of metal or plastics material. It presents a length of about 2 centimeters.

As can be seen in FIG. 1, the first and second longitudinal elements 4 and 6 are hinged to each other in their middle portions so as to constitute clip 8. On either side of a hinge pin 10, the clip 8 comprises a jaw 12 for holding an organ and means 14 for gripping the instrument and controlling the opening of the jaw 12. The longitudinal elements 4 and 6 are suitable for pivoting about the pin 10 between a closed position and an open position of the clip 8.

More precisely, the first longitudinal element 4 comprises in succession a pierced flat 16, a clevis 18, a connection shank 20, and a bearing disk 22. The flat 16 and the disk 22 extend in planes that are parallel but not coplanar. The clevis 18 extends the flat 16 towards the shank 20.

The second longitudinal element 6 is similar in shape to the first element 4. It thus likewise comprises a flat 24, a connection shank 26, and a bearing disk 28. Nevertheless, a convex projection 30 replaces the clevis 18. The convex projection 30 is engaged in the clevis 18. The pin 10 passes through the projection 30 and the clevis 18 to hinge the first element 4 to the second element 6.

The two flats 16 and 24 constitute the jaw 12 of the clip for holding an organ. They present anti-skid serrations 32 on their facing faces in order to make it easier to hold human or animal organs. In addition, the flats 16 and 24 include respective oblong through openings 34 extending over their entire length.

A spring 35 serves to hold the jaw 12 in a closed position and is mounted between the shanks 20 and 26. The spring 35 is suitable for exerting a pressure force suitable for bringing the flats 16 and 24 together. Thus, at rest, when no pressure is exerted on the outside surfaces of the bearing disks 22 and 28, the clip 8 is held in a closed or organ-pinching position. The spring 35 is formed by a metal blade secured to the shank 26 and bearing against the shank 20. The blade is suitable for exerting a force that opposes opening the clip.

The bearing disks 22 and 28 and the connection shanks 20 and 26 form means 14 for gripping and controlling opening of the jaw 12. They enable the anchor instrument to be handled and moved during a surgical operation.

The anchor instrument also comprises an arch 36 for attaching at least one traction element 37 to the clip 8. This traction element is preferably flexible. For example it may be constituted by a thread, a strip, a strap, etc. The traction thread 37 is suitable for being secured to the abdominal wall of the living being to be operated in order to raise and keep in suspension an organ held by the jaw 12. The thread may also carry an organ at a point situated between the clip and the parietal exit point of the thread, as described below in the method of using the anchor instrument of the invention.

The traction thread 37 is secured to the arch 36, e.g. by a flexible bond. The arch is secured at each end to the pin 10. The arch 36 is made of a semi-elastic material of the plastics material or rubber type, so that it deforms as a function of the direction in which the thread applies traction.

The arch 36 is positioned at a certain distance from the jaw 12 and the means 14 for gripping and controlling said jaw, so that the thread 37 does not wind about them. Furthermore, the arch 36 projects from the jaw 12 and the means 14 so as to make it easier to engage an additional traction thread during a surgical operation.

The means 14 also include projections 38 projecting from the outside surfaces 39 of the bearing disks 22 and 28 so as to make it easier to grip, handle, and control opening of the clip 8 using a conventional surgical forceps. Each projection 38 has a frustoconical end portion 40 and a cylindrical base 41 secured to the bearing disks 22, 28. The base 41 has a diameter that is slightly smaller than the diameter of the end windows in conventional surgical forceps so as to enable them to be inserted therein.

FIG. 3 shows a parietal anchor instrument in a second embodiment of the invention. This instrument is formed by a double hook 42. It comprises a rectangular support plate 43 having mounted thereon hook means 44, means 45 for attaching a traction thread 37, and means 46 for gripping the anchor instrument.

The hook means 44 comprise two hooks 47 and 48 projecting from one side of the plate 43 and both curved in the same direction.

The means 45 for attaching a traction thread comprise an arch 49 secured to the side opposite the side that presents the hooks 47 and 48.

The grip means 46 comprise two diverging and curved wings 50 and 51 that are secured to opposite faces of the plate 43 and that form a mean angle α relative to the plane thereof. The angle α is selected to facilitate gripping the instrument by means of surgical forceps regardless of the positioning of the double hook 42. This positioning is imposed by the location of the trocar and the position of the operating surgeon.

In a variant that is not shown, the hook means 44 for hooking an organ comprise a single hook or a triple hook.

The parietal anchor instruments shown in FIGS. 1 to 3 are example embodiments of the invention that are not limiting in any way. The shape of these instruments varies as a function of the type of organ that is to be held and as a function of its atraumatic nature.

In another variant of the first and second embodiments of the invention (not shown), the means 36 and 45 for attaching the traction thread are formed by an orifice passing through the anchor instrument. The thread is suitable for being inserted in the orifice and then attached around a wall of the instrument. For example, the orifice may be made through the convex projection 30 and the clevis 18, or through a connection shank 20, 26 of the clip 8. It may also be formed through the support plate 43.

Figure 5:
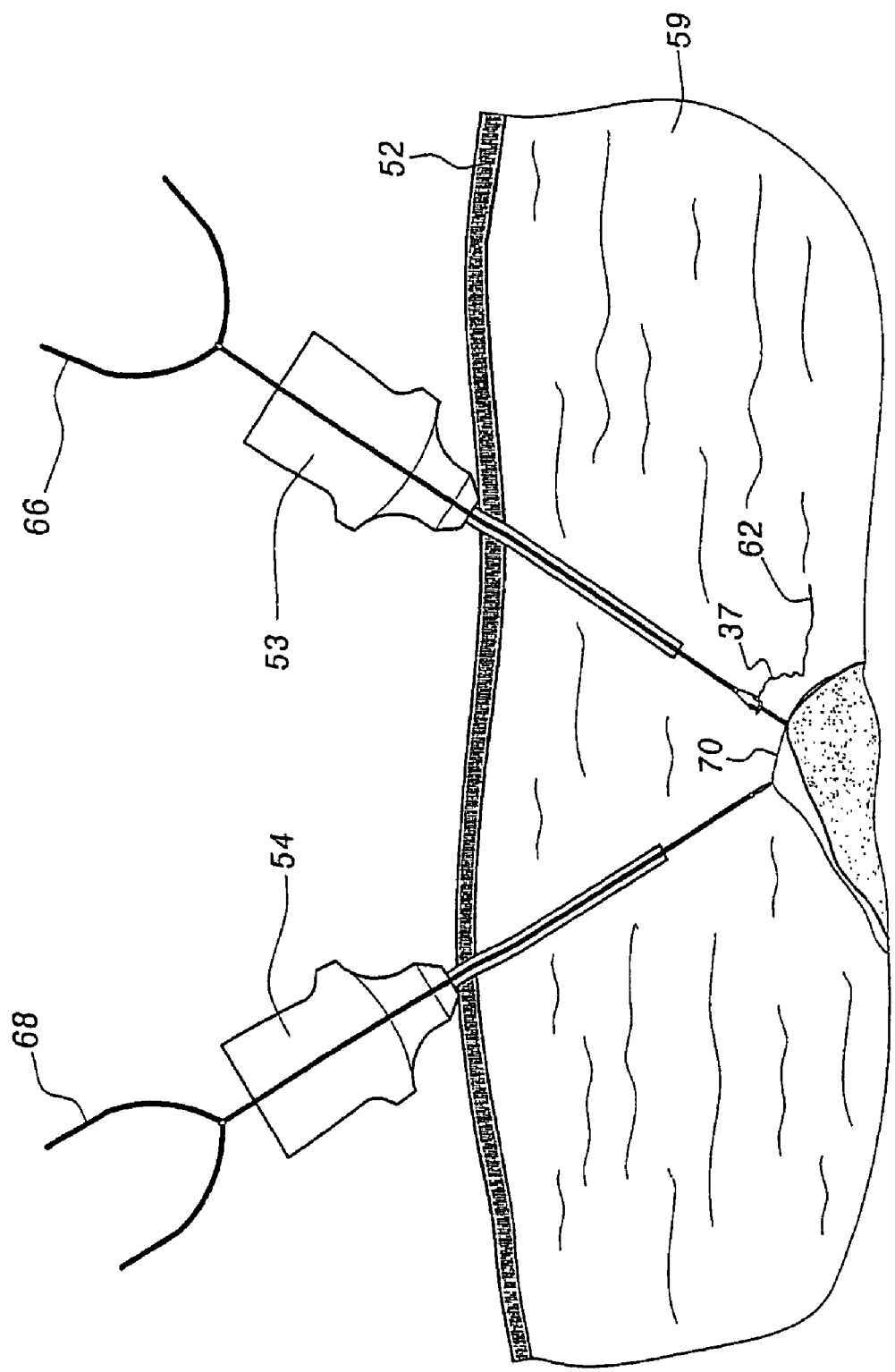
Figure 6:
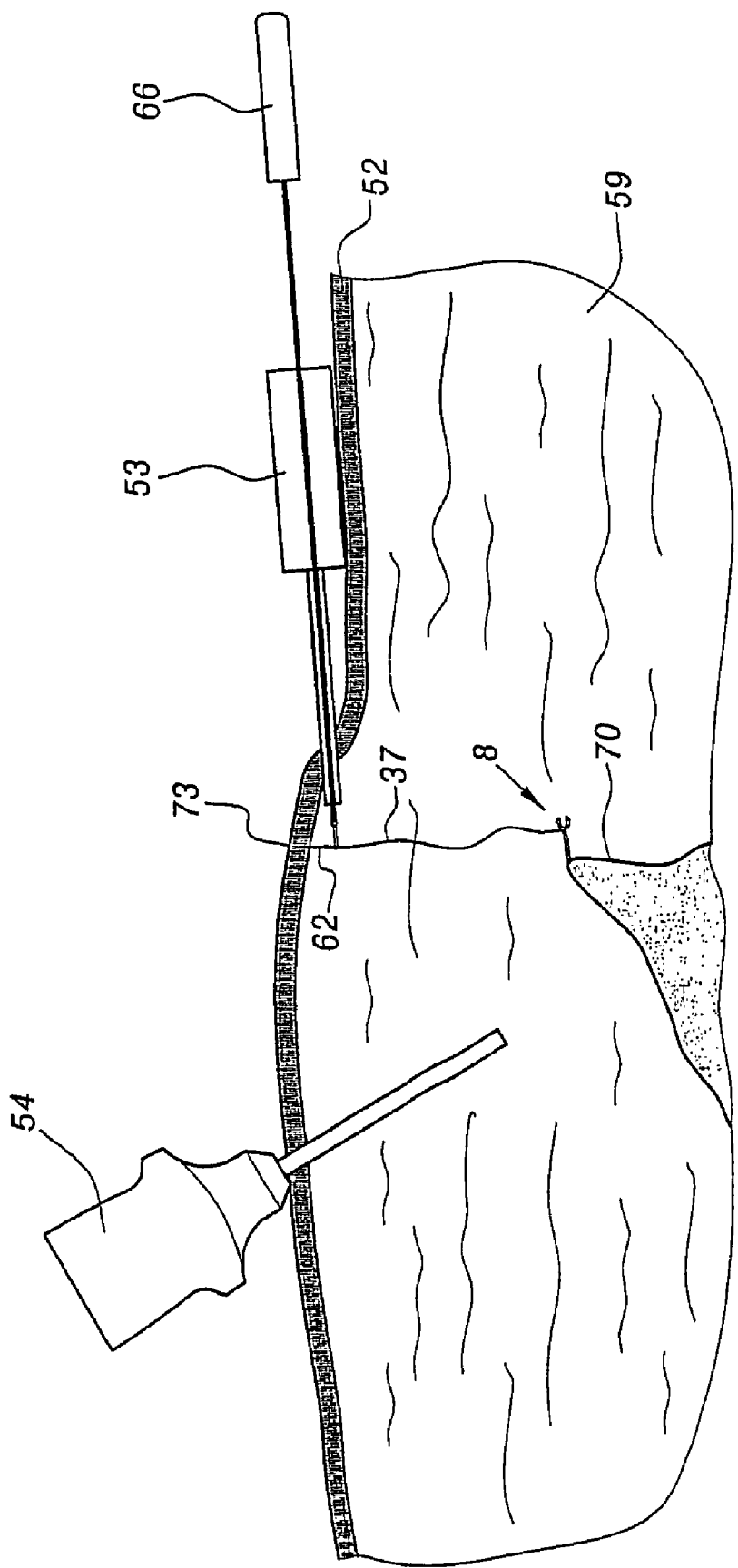

FIGS. 4 to 6 show a parietal anchoring method implemented using an anchor instrument constituting the first embodiment of the invention.

FIG. 4 is a diagrammatic section view of an operation space defined by an abdominal wall 52.

In a first step of the operation, two trocars 53 and 54 are inserted in the wall 52.

Then, during a second step of the operation, an anchor device 58 is brought via the trocar 53 into the operation space 59 of the abdomen. This device 58 comprises an anchor clip 8, a traction thread 37, and a needle 62. One end of the thread 37 is secured to the arch 36 of the clip 8. The other end of the thread 37 is secured to the needle 62.

In a third step of the operation, shown in FIG. 5, the surgeon introduces conventional forceps 66 and 68 into each of the trocars 53 and 54. The surgeon then moves out of the way an organ located in front of the anatomical region on which the operation is to be performed by using one of the forceps 68. This forceps takes hold of an organ 70 in order to expose the zone on which the operation is to be performed.

In order to hold the organ 70 away from the operation zone in a static position, the surgeon or the surgeon's assistant inserts the projections 38 of the grip and control means 14 of the clip 8 into the windows at the ends of the free forceps 66 or 68, opens the jaw 12 by using the grip and control means 14, and takes hold of the organ 70 in the jaws 12.

In a fourth step, shown in FIG. 6, the surgeon pierces the abdominal wall 52 with a needle 62 manipulated by the forceps 66 at a selected anchor point 73. The needle 62 and a portion of the thread 37 are thus moved out from the operation space 59. While this is taking place, the thread 37 pulls the organ 70 and the suspended clip 8 so that the organ 70 moves away from the operation zone.

Figure 7:
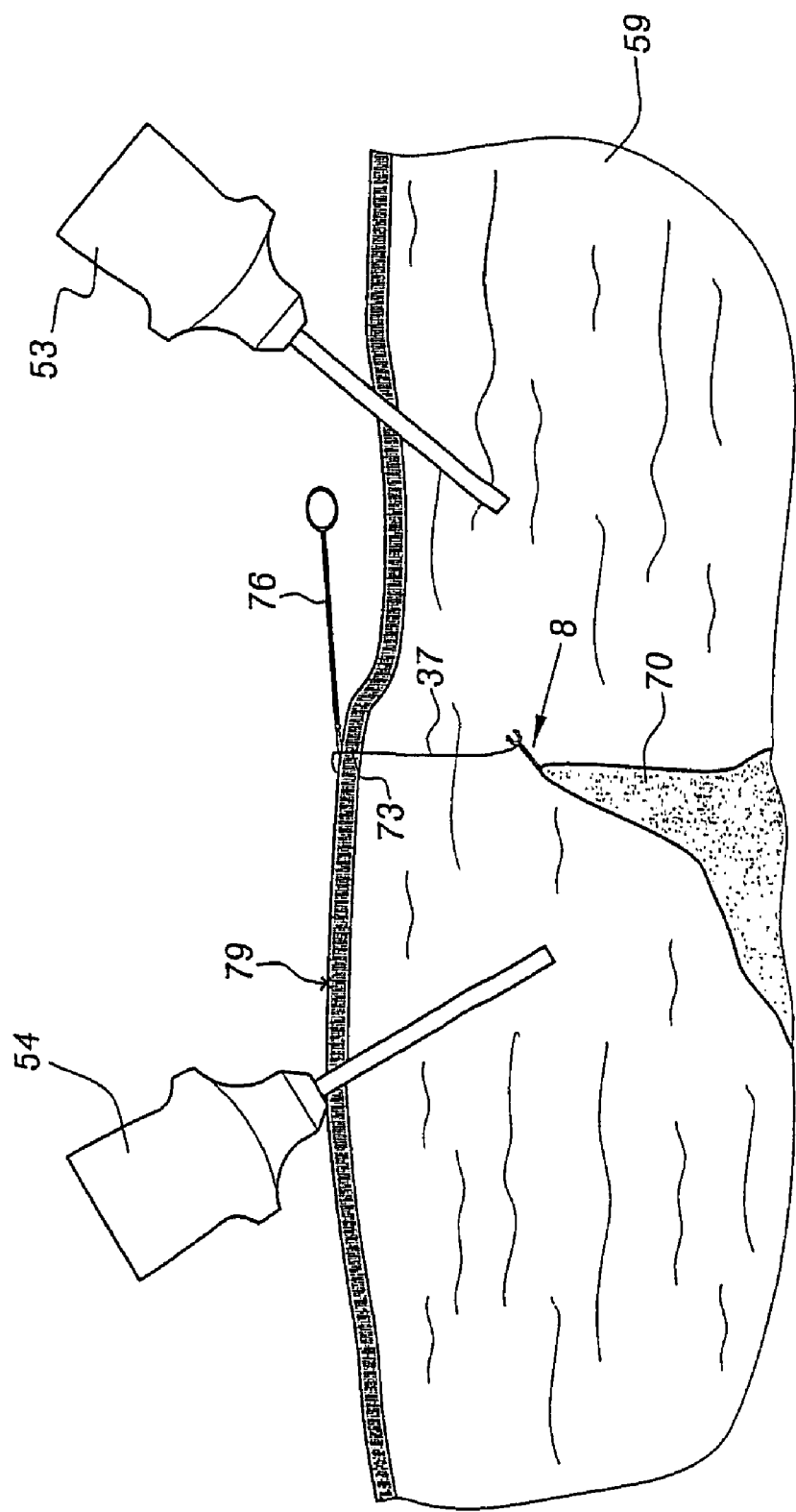

In a fifth step, shown in FIG. 7, the thread 37 is secured to the outside of the abdominal cavity 59 by fastener means 76, e.g. comprising a forceps. The thread 37 secured to the abdominal wall 52 thus constitutes a stationary anchor point 73 for the organ 70. The organ 70 is held away from the operation zone, but without being held by a surgeon's assistant or a robotic arm. The thread 3 maintains constant traction on the organ 70 without piercing it.

In a variant, the thread is attached inside the abdominal cavity to a transparietal intra-abdominal anchor system, i.e. an intraparietal fastener system connected to an extraparietal system that does not pass through a trocar. Under such circumstances, a plurality of traction threads can advantageously be attached to the intraparietal fastener system.

Advantageously, the position of the organ 70 can be readjusted during surgery merely by applying traction on the thread 37 outside the wall (or vice versa) and repositioning the fastener means 76.

A variety of anchor instruments 8, 42 of this type can be used simultaneously during surgery in order to optimize exposure and release the surgical forceps 66 and 68 that pass through the trocars 53 and 54 so as to enable them to perform dynamic roles during the operation.

Advantageously, the anchor instrument 8, 42 can be manipulated and moved during surgery so as to hold onto another organ in the abdominal cavity while maintaining the first anchor point 73 secured to the abdominal wall 52.

In parallel, the anchor point 73 of the organ can also be moved so as to obtain another viewing angle on the operation zone, while continuing to hold the organ 70 in the jaw 12. For example, when the surgeon seeks to orient the organ 70 in another direction, a second thread (not shown) can be inserted into the operation space 59, which thread is secured to the needle 62. The end of the second thread is secured to the arch 37 of the clip 8. Thereafter the previously attached first traction thread 37 is cut. The second thread is suitable for passing through the wall 50 with the help of the needle 62 at a second anchor point 79 different from the first anchor point 73.

Thus, the parietal anchor instrument makes it possible to hold an organ 70 in a certain position for a selected duration at a first anchor point, and then to move the organ 70 and to hold it suspended in a different orientation from a second anchor point 79.

The parietal anchor instrument thus makes it easier to expose an operation zone without requiring an additional trocar and without requiring an extra hand for acting thereon.

Advantageously, by reducing the number of trocars that are implanted, the number of incisions in the abdominal wall is reduced, thereby accelerating patient recovery by reducing the duration of post-operative convalescence.

The anchor instrument serves to reduce the number of surgeon's assistants needed to assist the surgeon during the operation, such that in the event of a hemorrhage or some other incident, a surgeon's assistant has an additional hand available for acting and dealing with the incident.

Advantageously, the gripping end of the clip 8 and the wings 50, 51 of the double hook 42 can be manipulated by conventional celioscopic instruments.

To recapitulate, the method of parietally anchoring an organ of a living being for exposing an anatomical structure that is to be treated during a surgical operation comprises:

a first step of inserting a trocar 53, 54 in the abdominal wall 52 of a human being or an animal;

a second step of introducing a parietal anchor instrument 8, 42, a needle 62, and at least one traction thread 37 into the abdominal cavity 59, a first end of the thread 37 being connected to the needle 62 and a second end of the thread 37 being connected to the anchor instrument 8, 42;

a third step of releasably holding said organ 70 by means of the anchor instrument 8, 42, which anchor instrument is suitable for taking hold of different organs in succession during an operation;

a fourth step of transpiercing the abdominal wall 52 from the inside to the outside by means of the needle 62, or of attaching to a transparietal intra-abdominal anchor system, and then pulling said organ 70 by means of the anchor instrument 8 and the thread 37; and a fifth step of securing the first end of the thread 37 to the outside of the abdominal wall 52 with the help of fastener means 76 so as to form a stationary anchor point 73, 79 for the organ held suspended by the thread and the anchor instrument.

This anchoring method is performed during a surgical operation. It is temporary. The organs held suspended by the thread and the anchor instrument are released at the end of the surgery.

The anchor instrument constituting the first embodiment of the invention serves to hold and pinch organs without piercing them or damaging them.

The invention claimed is:

1. A method of parietally anchoring an organ of a living being for exposing an anatomical structure that is to be treated during a surgical operation using laparoscopy or celioscopy, the method comprising:

a first step of inserting at least one trocar in the abdominal wall of said being;

a second step of introducing through the trocar a parietal anchor instrument, a needle, and at least one traction thread into the abdominal cavity, a first end of the thread being connected to the needle and a second end of the thread being connected to the anchor instrument;

a third step of releasably holding said organ by means of the anchor instrument, wherein said anchor instrument is suitable for taking hold of different organs in succession during an operation;

a fourth step of introducing a surgical forceps through one said trocar and gripping the needle by said forceps within said abdominal cavity, a fifth step of transpiercing the abdominal wall by means of the needle manipulated by said forceps, said transpiercing being performed in a transpiercing direction from a inside side to an outside side of said abdominal wall, and then pulling said organ from the outside of said abdominal wall, by means of the thread and the anchor instrument;

a sixth step of securing the first end of the thread to an outer face of the abdominal wall with the help of fastener means so as to form a stationary anchor point for the organ held suspended by the thread and the anchor instrument;

performing said surgical operation; and releasing said anchor instrument from said organ, wherein the parietal anchor instrument comprises:

holding parts for releasably holding said organ;

attachment means for attaching said at least one traction thread to said holding parts so that said second end of the thread is connected to the anchor instrument; and gripping and manipulation means for gripping and manipulating said holding parts with said forceps, wherein said holding parts comprise two longitudinal elements hinged to each other about a middle hinge pin to form a clip, and said clip comprises said holding parts on one side of the hinge pin and said gripping and manipulating means on the other side of said hinge pin, wherein said attachment means comprises an arch for attaching said at least one traction thread to said clip, said arch being positioned at a distance from said two longitudinal elements and from said gripping and manipulating means.

2. The method according to claim 1, wherein said gripping and manipulating means comprise two bearing disks, each bearing disk being provided with a single projection on an outside face thereof, and when the clip is gripped by said forceps, the two bearing disks are positioned with respect to distal ends of said forceps by the cooperation of each projection.

3. The method according to claim 1, wherein said arch is secured at each end thereof to said pin.

4. The method according to claim 1, wherein said arch is made of a plastic or rubber material which deforms as a function of a traction direction of said thread.

* * * * *